United States Patent
Nieters et al.

(10) Patent No.: US 9,638,344 B2
(45) Date of Patent: May 2, 2017

(54) SYSTEM AND METHOD TO MONITOR CHARACTERISTICS OF AN OPERATING FLUID IN A PROCESS LINE

(71) Applicant: Dresser, Inc., Addison, TX (US)

(72) Inventors: Edward James Nieters, Burnt Hills, NY (US); Frederick Wilson Wheeler, Niskayuna, NY (US); Harold Randall Smart, Portsmouth, RI (US)

(73) Assignee: Dresser, Inc., Addison, TX (US)

( * ) Notice: Subject to any disclaimer, the term of this patent is extended or adjusted under 35 U.S.C. 154(b) by 119 days.

(21) Appl. No.: 14/084,238

(22) Filed: Nov. 19, 2013

(65) Prior Publication Data

US 2015/0136247 A1 May 21, 2015

(51) Int. Cl.
*F15B 19/00* (2006.01)
*F16K 31/12* (2006.01)
*G01N 33/00* (2006.01)
*F15B 21/04* (2006.01)

(52) U.S. Cl.
CPC ............ *F16K 31/12* (2013.01); *F15B 19/005* (2013.01); *G01N 33/0009* (2013.01); *F15B 21/048* (2013.01); *Y10T 137/7722* (2015.04); *Y10T 137/7762* (2015.04); *Y10T 137/8158* (2015.04)

(58) Field of Classification Search
CPC ...... F16K 31/12; F15B 19/005; F15B 21/041; F15B 21/048; G01N 33/0009; Y10T 137/8158; Y10T 137/8326; Y10T 137/776; Y10T 137/7762
USPC .............. 251/28, 331, 129.04; 356/335–343, 356/432–441, 445–448
See application file for complete search history.

(56) References Cited

U.S. PATENT DOCUMENTS

| | | | |
|---|---|---|---|
| 4,494,568 A | * | 1/1985 | Young ........................ 137/561 A |
| 4,573,344 A | | 3/1986 | Ezekoye |
| 4,901,751 A | | 2/1990 | Story et al. |

(Continued)

FOREIGN PATENT DOCUMENTS

| | | |
|---|---|---|
| CN | 1062971 A | 12/1991 |
| WO | 9506276 A1 | 3/1995 |

(Continued)

OTHER PUBLICATIONS

International Search Report and Written Opinion issued in connection with corresponding PCT Application No. PCT/US2014/066399 dated May 13, 2015.

(Continued)

*Primary Examiner* — Craig Schneider
*Assistant Examiner* — Josephine Trinidad-Borges
(74) *Attorney, Agent, or Firm* — Paul Frank + Collins P.C.

(57) ABSTRACT

A system that provides localized monitoring of characteristics of instrument gas that a valve assembly uses to modulate the flow of a working fluid. The system includes components that generate an output in response to, for example, particulates, humidity, temperature, and other characteristics of the instrument gas. Processing of data and information in the output can help to diagnose changes in the characteristics of the instrument gas. This diagnosis is useful to predict a time frame during which the valve assembly and components associated therewith might fail and/or require maintenance before the valve assembly manifests significant problem that are detrimental to a process line.

18 Claims, 11 Drawing Sheets

(56) References Cited

U.S. PATENT DOCUMENTS

| | | | |
|---|---|---|---|
| 5,231,469 A | | 7/1993 | Jeffers et al. |
| 5,316,035 A | | 5/1994 | Collins et al. |
| 5,538,036 A | * | 7/1996 | Bergamini et al. ............ 137/552 |
| 5,758,686 A | * | 6/1998 | Ohtsuka et al. ............ 137/492.5 |
| 5,939,727 A | * | 8/1999 | Sommer ........................ 250/573 |
| 6,026,834 A | * | 2/2000 | Azima .................. G05D 7/0635 137/1 |
| 6,298,377 B1 | | 10/2001 | Hartikainen et al. |
| 6,601,005 B1 | | 7/2003 | Eryurek et al. |
| 6,763,703 B2 | | 7/2004 | Krieger et al. |
| 2011/0130882 A1 | * | 6/2011 | Perez .................. G01N 33/2835 700/282 |
| 2011/0240891 A1 | * | 10/2011 | Inagaki ...................... 251/30.01 |
| 2011/0315904 A1 | | 12/2011 | Karte |
| 2012/0041582 A1 | | 2/2012 | Wallace |
| 2013/0079895 A1 | | 3/2013 | Hedtke |

FOREIGN PATENT DOCUMENTS

| | | |
|---|---|---|
| WO | 9738254 A1 | 10/1997 |
| WO | 9905576 A2 | 2/1999 |
| WO | 0248686 A2 | 6/2002 |

OTHER PUBLICATIONS

Harold Randall Smart, Aug. 7, 2013, U.S. Appl. No. 13/961,335.
Office Action issued in corresponding Chinese Patent Application Serial No. 201480063338.X dated Dec. 1, 2016.

* cited by examiner

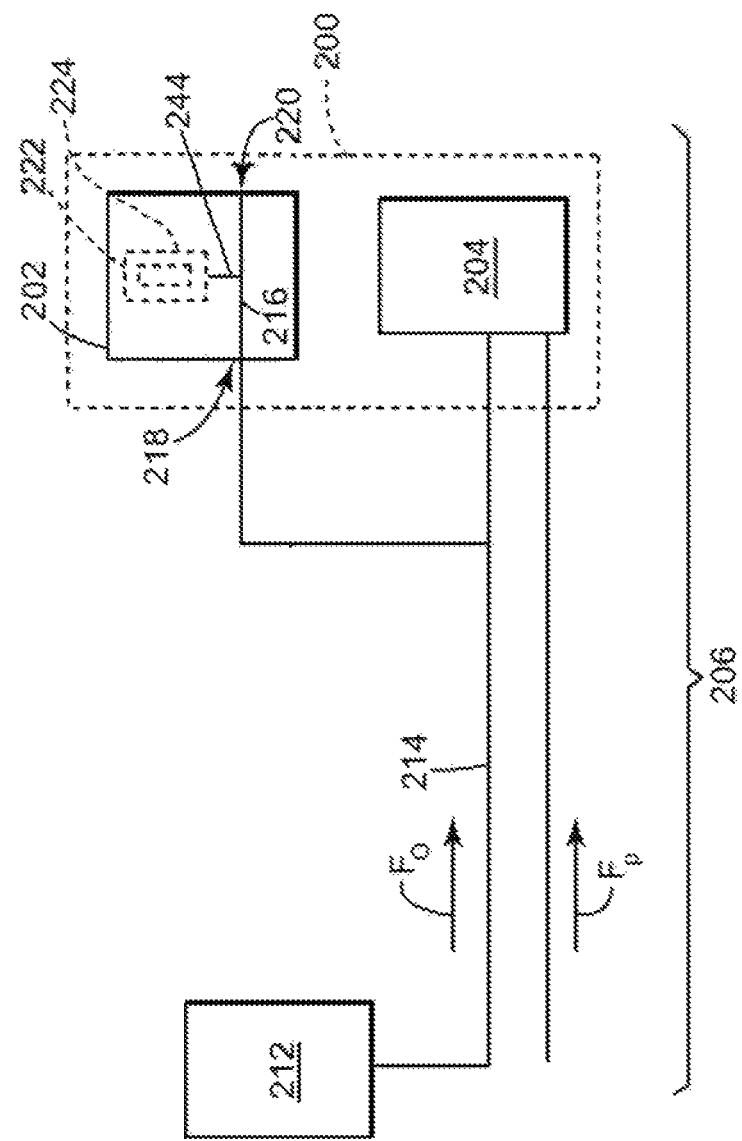

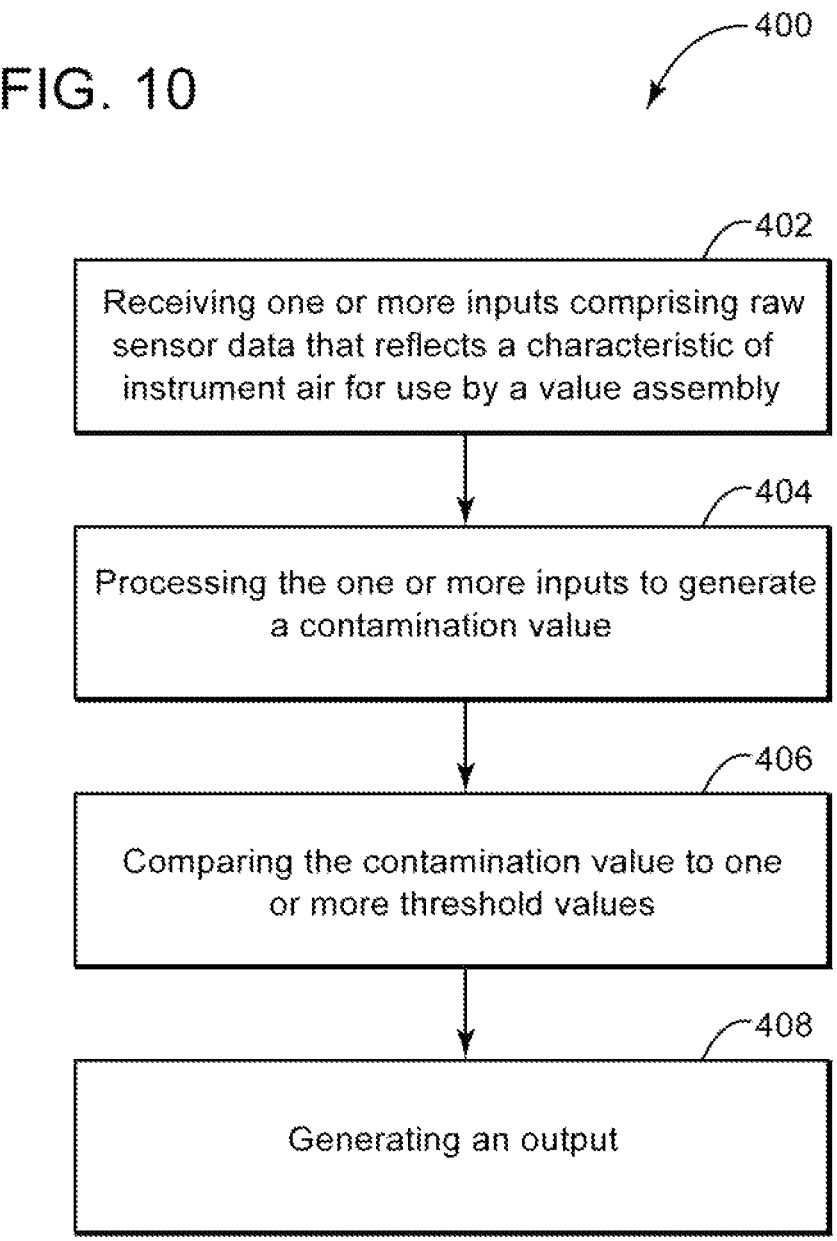

SYSTEM AND METHOD TO MONITOR CHARACTERISTICS OF AN OPERATING FLUID IN A PROCESS LINE

BACKGROUND

The subject matter disclosed herein relates to industrial processes, process facilities, and device diagnostics, with particular discussion below that concerns the quality of gasses that these facilities use to operate certain devices (e.g., control valves) found on the process line.

Industrial process facilities that operate processes may utilize many varieties of flow controls that regulate a flow of process fluids (e.g., gas and liquid). Problems with these devices can often disrupt the process. These disruptions can lower yields and reduce quality. Also, in large refineries, chemical plants, and power plants, technicians may need to troubleshoot and repair the problematic devices. The service on the devices can lead to significant expense from process downtime and other collateral issues.

Devices for use as the flow controls include valve assemblies that operate under the influence of an operating fluid, namely, compressed or pressurized gas ("instrument gas"). Often, the facility includes a fluid delivery system with a source (e.g., a compressor) and lines (e.g., tubing) that plumb the valve assemblies to the compressor. This fluid delivery system delivers the instrument gas under pressure to the valve assembly. In conventional configurations, the valve assembly has a pneumatic actuator, which utilizes the instrument gas to change the position of a plug relative to a seat, thereby modulating the flow of the process fluid through the valve assembly. The valve assembly can also incorporate electrical and/or electro-pneumatic components to regulate the flow of the instrument gas into the pneumatic actuator.

Some of the components in the valve assembly, including the electrical and electro-pneumatic components, are sensitive to characteristics of the instrument gas. These characteristics include, for example, levels of contaminants, relative humidity, temperature, and the like. Specifications for the valve assembly may set out appropriate levels and/or operating ranges for the characteristics of the instrument gas. These levels define the "quality" of the instrument gas that may help maintain the operation of the valve assembly. Deviation of the characteristics from these levels, however, may expose the sensitive components in the valve assembly to instrument gas that can degrade performance and, eventually, can lead to problematic operation of the valve assembly that requires repair and/or replacement of the valve altogether.

The fluid-delivery system may employ safeguards to maintain the characteristics of the instrument gas at or near the levels set out for operation of the valve assembly. The safeguards may include, for example, conditioning devices (e.g., filters, scrubbers, humidifiers, de-humidifiers, heaters, chillers, etc.). These devices condition the instrument gas to meet the specifications for use by the valve assemblies.

In many conventional applications, the conditioning devices reside at locations remote, and often far removed, from the valve assemblies that receive the instrument gas. These locations afford the fluid delivery system with little in the way to protect against changes in the characteristics that may occur downstream of the conditioning devices. For example, particulates and other contaminants (e.g., lubricants and oils) may enter the lines that transfer the instrument gas between the conditioning device and the valve assembly. Moreover, maintenance and/or other system-level services on the fluid delivery systems can introduce moisture that changes the relative humidity of the instrument gas that enters the valve assembly.

This moisture, and other contaminants, can transit through the fluid delivery system to the components of the valve assembly. Unfortunately, conventional arrangements of fluid delivery systems often lacks appropriate feedback downstream of the conditioning devices to detect changes in the characteristics of the instrument gas. This oversight does not allow facility operators to appreciate, for example, particle accretion into the instrument gas downstream of filters, let alone to provide data that reflects the characteristics of the instrument gas found locally at and/or near the valve assemblies on the process line.

BRIEF SUMMARY OF THE INVENTION

The subject matter of this disclosure improves feedback about the characteristics of the instrument gas to avoid problems with the valve assembly. This disclosure describes embodiments of a system that monitors characteristics of the instrument gas in proximity to the valve assembly. In one implementation, the system may include components that generate an output with data that reflects, for example, levels of particulates, humidity, temperature, and other characteristics of the instrument gas local to the valve assembly. The embodiments can use this data to identify potential problems or to deliver the data to a control device, often referred to as an asset management system, that is in communication with the control structure that operates the process line. The asset management system can process the data to diagnose changes in the characteristics of the instrument gas. This diagnosis is useful to predict a time frame during which the valve and components associated therewith might fail and/or require maintenance before the valve assembly manifests significant problem.

BRIEF DESCRIPTION OF THE DRAWINGS

Reference is now made briefly to the accompanying figures, in which:

FIGS. 6 and 6A depict a schematic diagram of installations for the measurement module of FIG. 2 in the system of FIG. 1;

FIG. 10 depicts a flow diagram of an exemplary embodiment of a method for monitoring quality of instrument gas for use by valves on a process line.

Where applicable like reference characters designate identical or corresponding components and units throughout the several views, which are not to scale unless otherwise indicated.

DETAILED DISCUSSION

Figure 1:
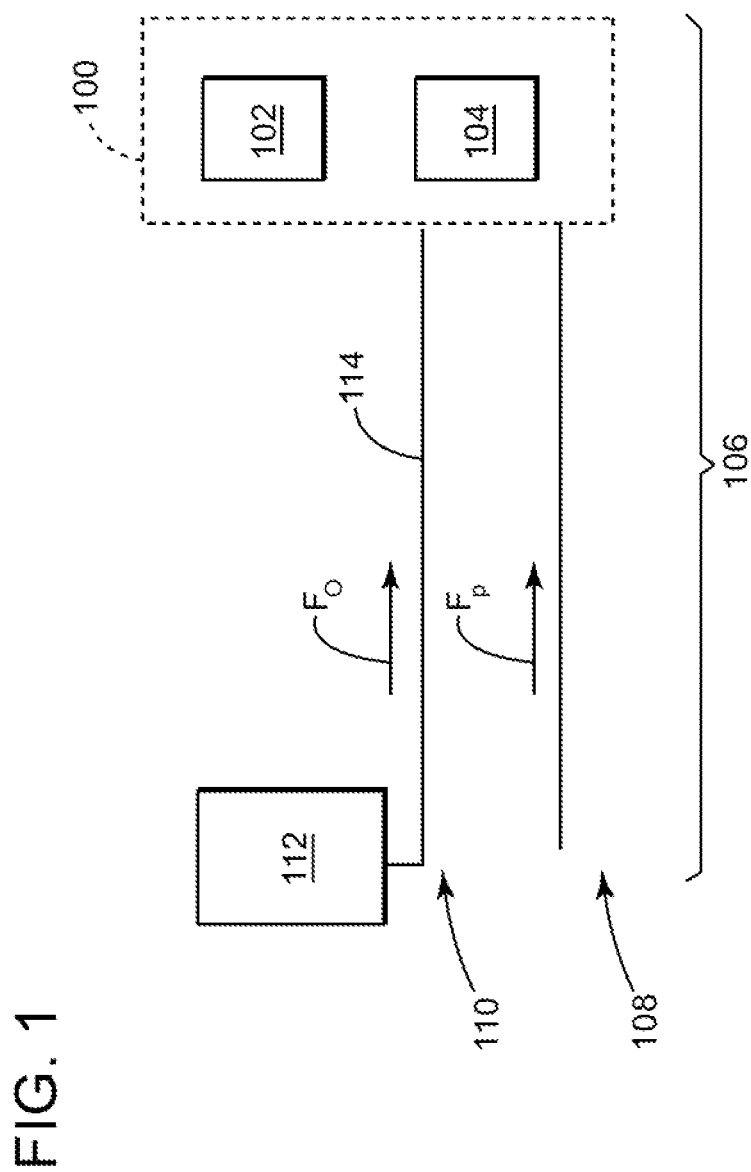
FIG. 1 depicts a schematic diagram of an exemplary embodiment of a system to monitor characteristics of an operating fluid for use by a valve.

FIG. 1 depicts a schematic diagram of an exemplary embodiment of a system 100 for monitoring quality of an operating fluid (e.g., liquids and gases) for use to operate devices in a process facility or plant. The system 100 has one or more components including, for example, a measurement module 102 and a valve assembly 104. These components integrate with a process line 106 that has a first fluid delivery system 108 and a second fluid delivery system 110. The first fluid delivery system 108 transfers a process fluid $F_P$ to the valve assembly 104. Examples of the process fluid $F_P$ include crude oil (for refining), chemicals, and other materials that are the subject of the process on the process line 106. The second delivery system 110 has a supply 112 (also "source 112") and one or more supply lines 114. Together these components distribute an operating fluid $F_O$ to the components of the system 100, as well as throughout the various implements found on the process line 106 and around the process facility or plant. Unlike the process fluid $F_P$, however, examples of the operating fluid $F_O$ include gasses that are useful to operate the valve assembly 104. For example, the operating fluid $F_O$ can embody pressurized gas (also, "instrument gas") that operates an actuator on the valve assembly 104 to modulate flow of the process fluid $F_P$ in accordance with parameters set out for the process on the process line 106.

As discussed more herein, the system 100 can monitor changes in the characteristics of the instrument gas. The measurement module 102 can include sensors and like components that can generate an output that conveys data and information about the characteristics of the instrument gas. Changes in the characteristics can manifest in several ways; for example, particulates and/or other contaminants can enter the instrument gas between the source 112 and the valve assembly 104. Use of the measurement module 102 can collect information about these changes, which are generally not available in conventional process lines and facilities that utilize conditioning devices remote from the valve assembly 104. This data collection affords the system 100 with feedback as to the quality of the instrument gas the valve device 104 utilizes to modulate flow of the process fluid $F_P$. Further processing of this information can identify the potential for the valve assembly 104 to develop problems and, importantly, allow for action that can remediate the problems before the onset of potential failure of the valve assembly 104.

The system 100 collects samples of the instrument gas in a location near, or in proximity to, the valve assembly 104. This location ensures that the information reflects conditions of the instrument gas that are local to the valve assembly 104. For example, the measurement module 102 may collect samples of the instrument gas from the second delivery system 110 upstream of and within one to two feet of the valve assembly 104. In other examples, sample collection occurs just upstream of sensitive components (e.g., electrical components and mechanical components) of the valve assembly 104. During data processing, the proximity of the samples can allow for specific, individualized understanding about the impact that changes in characteristics of the instrument gas can have on operation of the valve assembly 104.

Construction of the system 100 can locate the measurement module 102 variously to provide these samples to assess the local characteristics, or local qualities, of the instrument gas. The measurement module 102 can form part of the valve assembly 104, securing to and/or integrating with structures to afford a physical connection with the valve assembly 104. In other examples, the measurement module 102 forms a separate piece (or assembly) that secures to components found on the process line 106. This configuration can position the measurement module 102 remote from the valve assembly 104, but in communication with the supply line 114 to collect samples of the instrument gas in proximity to the valve assembly 104. As noted more below, embodiments of the system 100 can also provide a connection that allows for the exchange of data, power, and/or electrical signals between the measurement module 102 and the valve assembly 104. This connection can utilize one or more wires; although this disclosure contemplates configurations that utilize wireless connections to facilitate the exchange of data.

Figure 2:
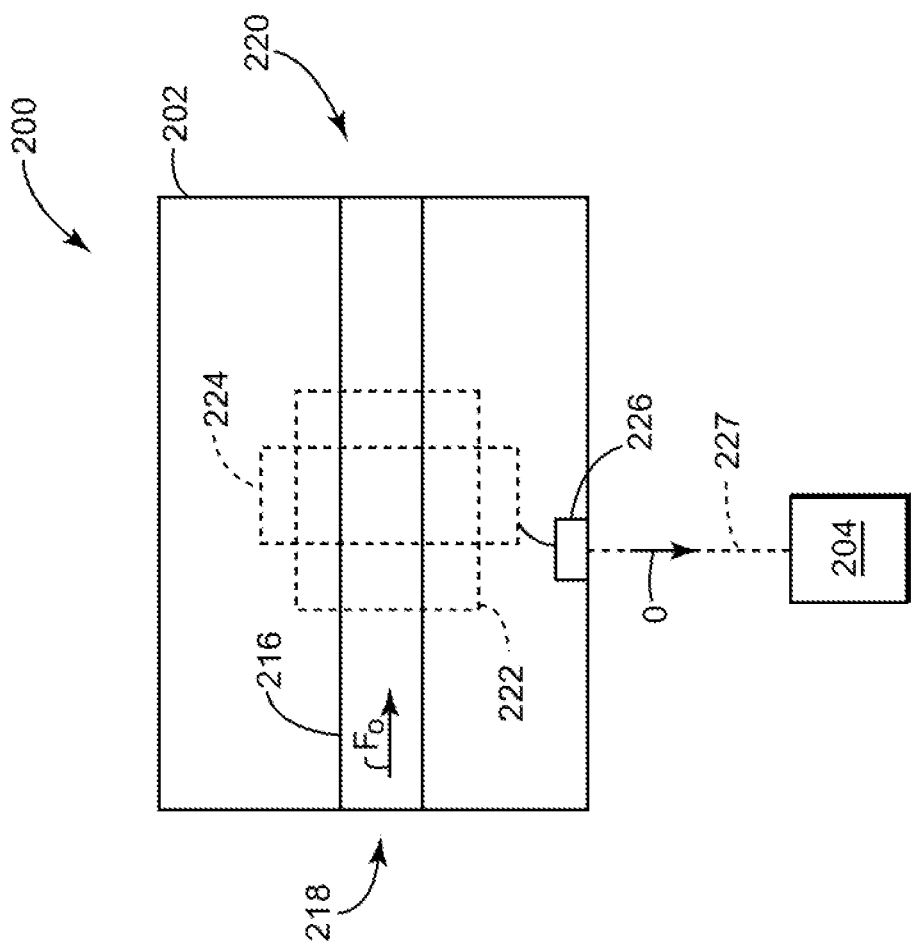
FIG. 2 depicts a schematic diagram of an example of a measurement module that finds use in the system of FIG. 1.

FIG. 2 depicts a schematic diagram of an exemplary embodiment of a system 200. The measurement module 202 includes a flow pathway 216 with an inlet 218, an outlet 220, and a chamber 222 disposed therebetween. A sensor component 224 couples with the chamber 222 and with an output component 226, which has a connection 227 that couples the output component 226 with the valve assembly 204 for the exchange of an output O.

The sensor component 224 includes devices that provide indication of contaminants (and other characteristics) found in the instrument gas that flows into the chamber 222. These devices may generate the output O, which reflects and/or defines characteristics of the instrument gas (e.g., humidity, temperature, particulate/contamination, etc.). In other examples, the output O may identify particular chemical signatures and/or makeup of the instrument gas.

As shown in FIG. 2, the output component 226 can receive the output O from the sensor component 224. The output component 226 can include one or more devices that can distribute the output O from the measurement module 202. These devices include connectors that couple the output O to peripheral components, e.g., a central controller and/or processing device that can process the data in the output O. This processing device may be found on the valve assembly 204. The output component 226 may also include transmitters (e.g., antenna) that wirelessly relay the output O to these peripheral components. Moreover, this disclosure contemplates construction of the measurement module 202 that incorporates one or more processors that have access to executable instructions, e.g., stored on memory either locally and/or remote from the measurement module 202. This configuration can afford the measurement module 202 with capabilities to process data in the output O and, thus, render feedback as to one or more characteristics of the instrument gas.

The measurement module 202 can also include a housing that encloses one or more of the components identified above. This housing can have a unitary structure formed monolithically from a single piece of material (e.g., aluminum, steel, plastics, composites, etc.). Alternative constructions may incorporate multiple pieces that assemble together to create and secure the housing with the components of the measurement module 202. As discussed more in connection with FIG. 8 below, one or more of the components of the measurement module 202 may integrate inside of a valve positioner, which houses hardware and components that operate an actuator of the valve assembly 204 to modulate flow of the process fluid $F_P$. This construction can forgo use of the housing; instead, the various components secure with and/or within the structures of the valve positioner.

The flow pathway 216 conducts the instrument gas between the inlet 218 and the outlet 220, via the chamber 222. This construction directs the instrument gas proximate the sensor component 224. Examples of the flow pathway 216 can form integrally with the housing (e.g., as a bore or hole). In one example, the flow pathway 216 comprises a tube and/or conduit that couples with the inlet 218 and the outlet 220.

The chamber 222 provides an area for the sensor component 224 to interrogate the instrument gas. The chamber 222 can have geometry set out by the parts of the flow pathway 216. The geometry can be cylindrical if, for example, the constructive elements of the flow pathway 216 are cylindrical, e.g., as a bore and/or tubular element. In other embodiments, the geometry may conform to any variety of shapes and sizes; the configuration of the chamber 222 may, for example, form an enlarged volume in the central portion of the measurement module 202 that couples with the flow pathway 216 on either end.

The sensor component 224 can secure proximate the chamber 222 to permit access to the instrument gas. Examples of the sensor component 224 include devices that generate outputs in response to one or more characteristics of the instrument gas. These devices include, for example, electronic devices (e.g., transducers, thermistors, thermocouples, capacitive devices, etc.) that can generate signals (including digital signals and analog signals). Other examples of these devices may utilize a source of ionizing radiation that ionizes the chamber 222. Contaminants that enter the chamber 222 will disrupt the current in the chamber 222, which indicates the presence of contaminants. The devices can also include opto-electronic sensors, which can have a source and a detector. These types of sensors use light beams to evaluate the presence of particulate matter in the instrument gas.

Figure 3:
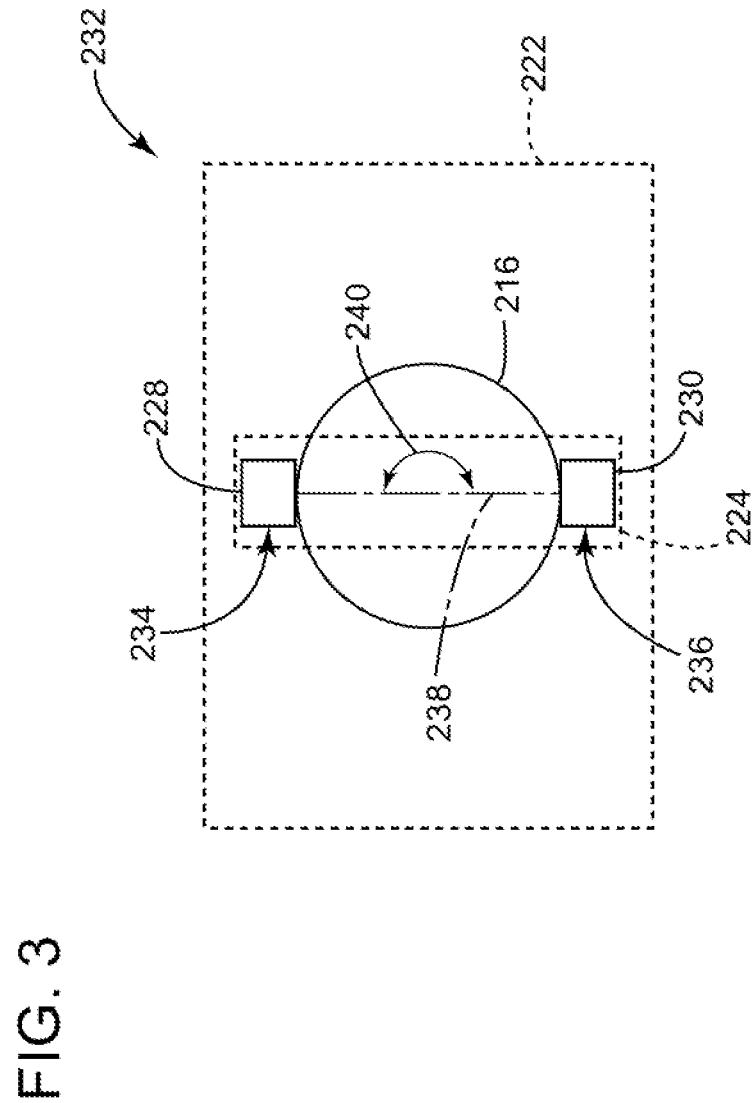
FIG. 3 depicts a schematic diagram of a sensor component having sensor elements in a first configuration for use in the measurement module of FIG. 2.
Figure 4:
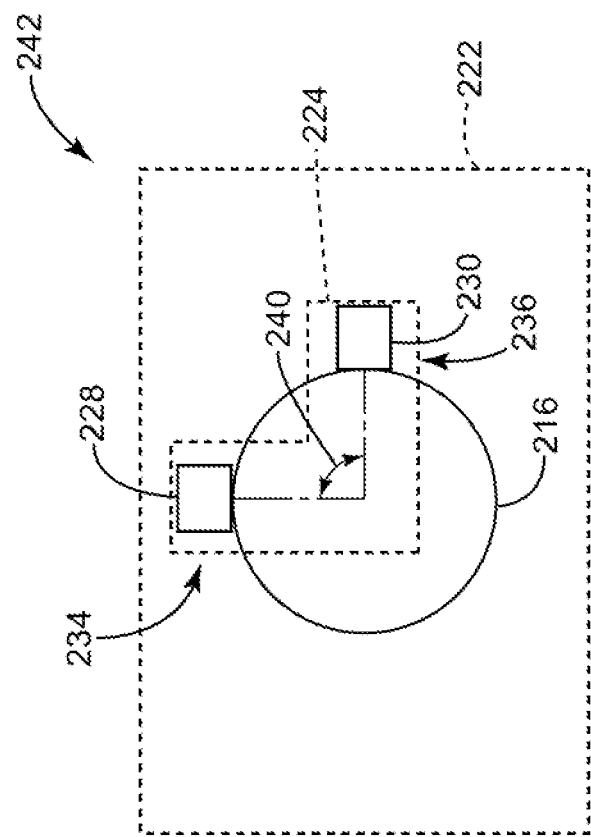
FIG. 4 depicts a schematic diagram of a sensor component having sensor elements in a second configuration for use in the measurement module of FIG. 2.

FIGS. 3 and 4 illustrate configurations for the sensor component 224 that utilize source/detector components to monitor particulate matter in the instrument gas. In FIG. 3, the sensor component 224 includes one or more sensor elements (e.g., a first sensor element 228 and a second sensor element 230). The sensor elements 228, 230 assume a first configuration 232 with the first sensor element 228 and the second sensor element 230 in positions (e.g., a first position 234 and a second position 236) that describe an axis 238, or a line-of-sight, that extends through at least a portion of the chamber 222. The axis 238 forms an observation angle 240, which in the present example is approximately 180°.

Examples of the sensors elements 228, 230 can utilize light to detect the characteristics of the instrument gas. The sensor elements 228, 230 can include a light source component that generates a beam of light and a detector component that generates signals in response to the beam. During operation, contaminants in the instrument gas that cross proximate the axis 238 may break the beam that traverses the chamber 222 from the source component to the detector component. The sensor component 224 can generate the output O (FIG. 2) in response to the breaks that occur in the beam. For instrument gas that is clean (e.g., with few contaminants), light from the source will fall uninterrupted on the detector for long periods of time. Contaminants found in the instrument gas will cause more (and/or longer and/or more frequent) disruptions in the beam, thus indicating the presence of one or more particles in the instrument gas.

FIG. 4 shows the sensor elements 228, 230 in a second configuration 242 in which the observation angle 240 is less than approximately 180°. In one example, the sensor elements 228, 230 are orthogonal to one another, forming an observation angle 240 of approximately 90°. This configuration locates the sensor component and the detector component in positions so the beam of light from the source component does not fall directly on the detector component. During operation with instrument gas that is clean (e.g., with few contaminants), the light from the source component passes through the chamber 222, but fails to fall on the detector component. As the number (and/or concentration) of contaminants increases, however, the contaminants can reflect light from the source component in the direction of the detector component to allow the beam of light to fall onto the detector component, thus indicating the presence of one more or contaminants in the instrument gas.

Figure 5:
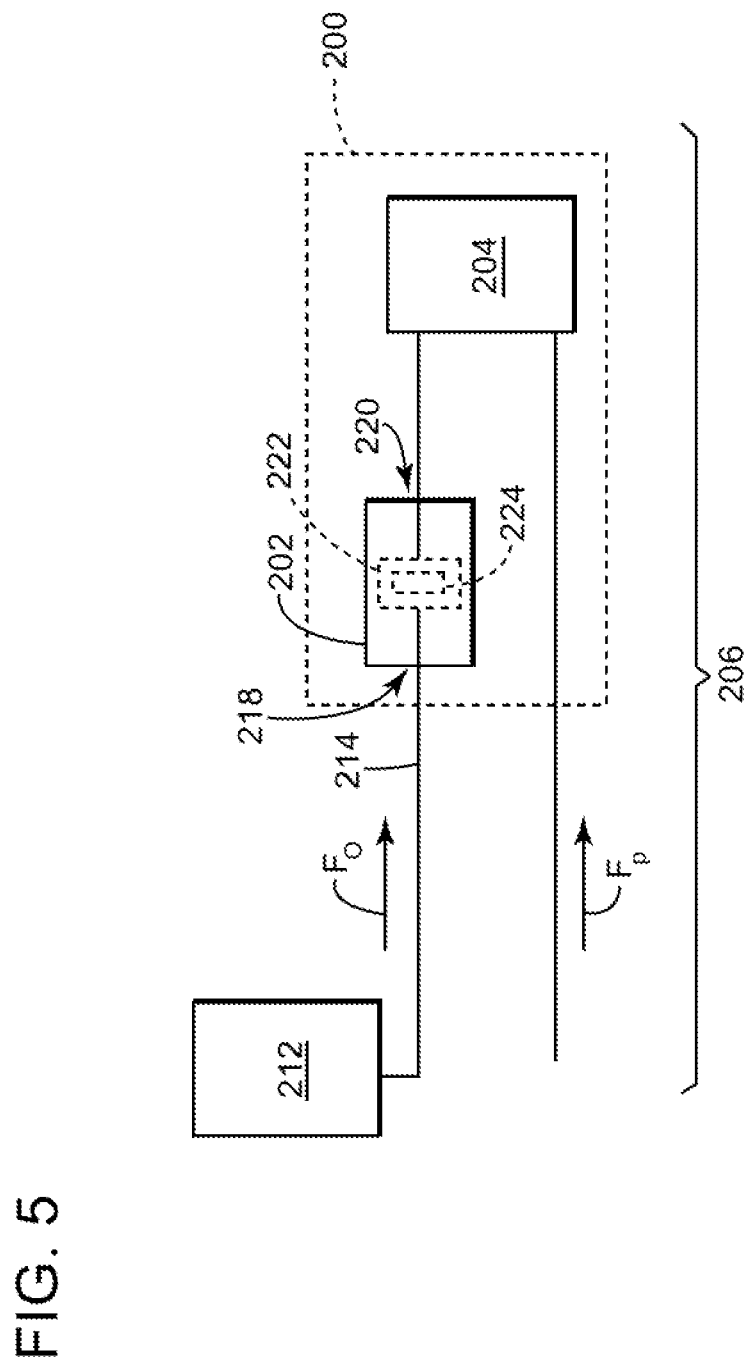
FIG. 5 depicts a schematic diagram of one installation for the measurement module of FIG. 2 in the system of FIG. 1.
Figure 6:
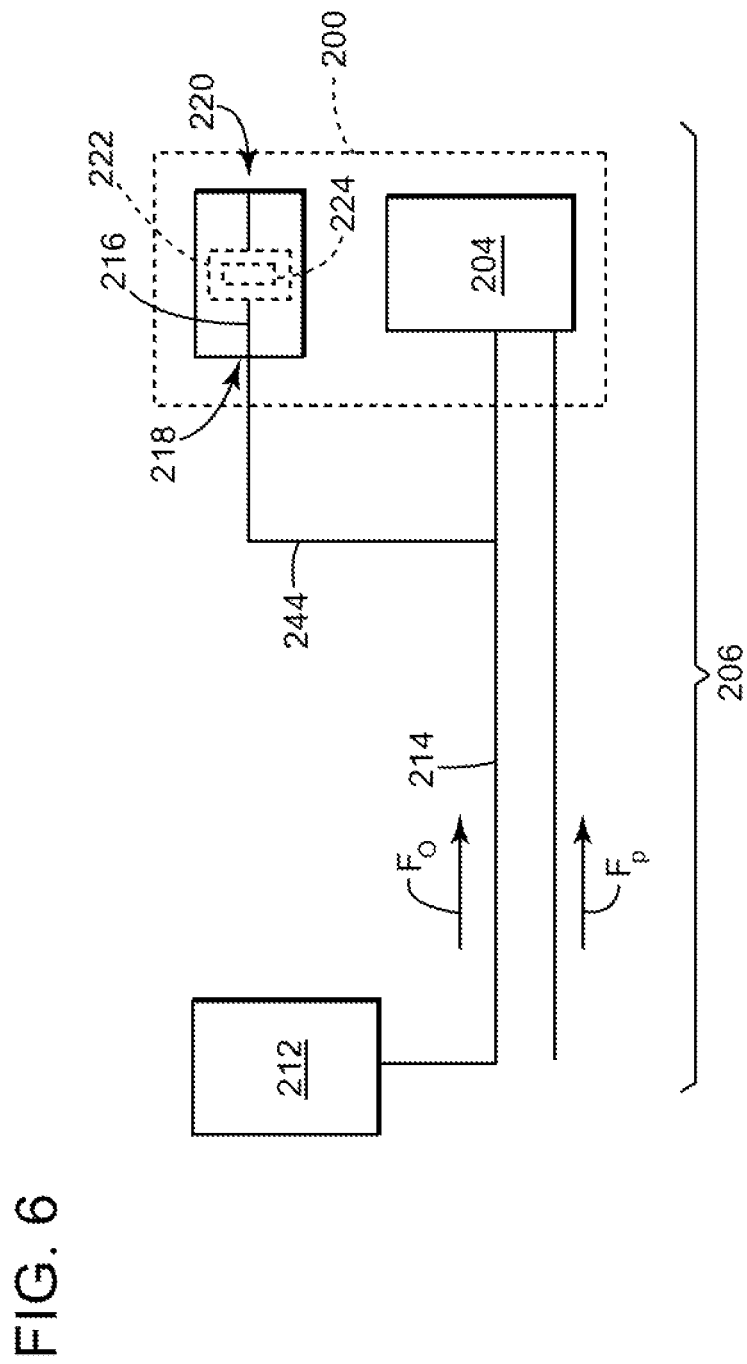

FIGS. 5 and 6 illustrate different installations of the system 200 as part of the process line 206. The installation of FIG. 5 positions the measurement module 202 in-line with the supply line 214, coupling the measurement module 202 with the supply line 214 at both the inlet 218 and the outlet 220. This construction directs the instrument gas through the chamber 222 and in proximity to the sensor component 224. The installation of FIG. 6 incorporates a sample line 244 that couples the inlet 218 on the module 202 with the supply line 214. The use of the sample line 244 directs, or draws off, a sample of the instrument gas to the measurement module 202. During operation, the sample flows into the chamber 222 proximate the sensor component 224. The outlet 220 allows the sample to exhaust, e.g., to the environment that surrounds the measurement module 202.

Although not shown, this disclosure contemplates use of one or more valves (e.g., a solenoid valve) that can regulate intake of samples of the operating fluid $F_O$ into the inlet 218. Moreover, as shown in FIG. 6A, this disclosure further contemplates that the measurement module 202 can incorporate the sample line 244, wherein the sample line 244 couples the chamber 222 with the flow pathway 216, rather than with the supply line 214. This configuration separates the chamber 222 from the flow pathway 216, which may avoid any adverse affects the chamber 222 and/or other features of the measurement module 202 may have on flow properties (e.g., flow rate, pressure, etc.) of the instrument gas.

As shown in FIGS. 5 and 6, the measurement module 202 couples with the supply line 214 upstream of the valve assembly 204. This upstream position of the measurement module 202 captures samples of the instrument gas to identify characteristics before the instrument gas interfaces with one or more components of the valve assembly 204. For example, the sample may occur upstream of an actuator that changes position in response to the instrument gas. In other examples, the sample may occur upstream of electrical components of the valve assembly 202 that are sensitive to contamination that might be found in the instrument gas.

Figure 7:
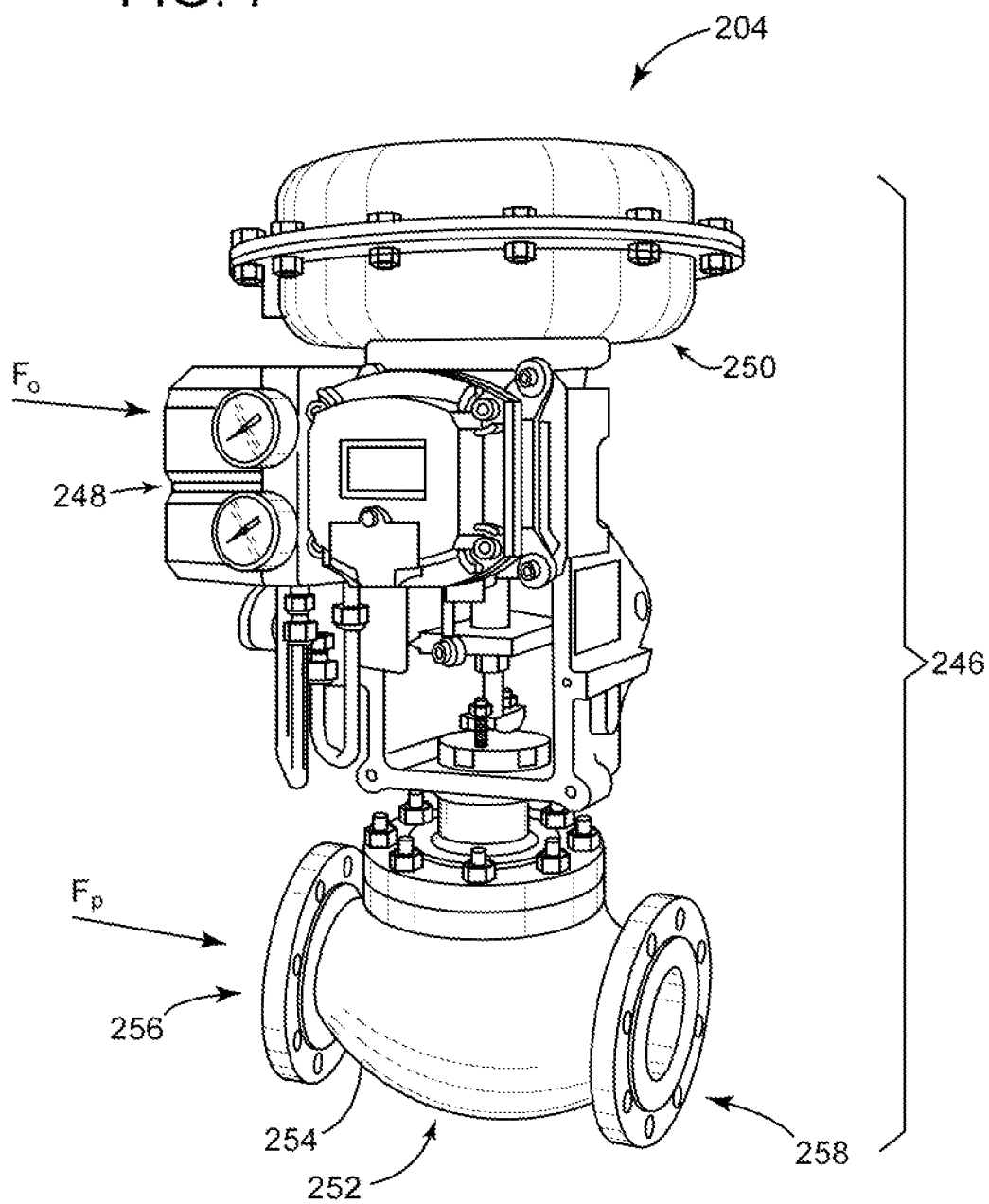
FIG. 7 depicts a perspective view of an example of a valve device for use in the system of FIG. 1.
Figure 8:
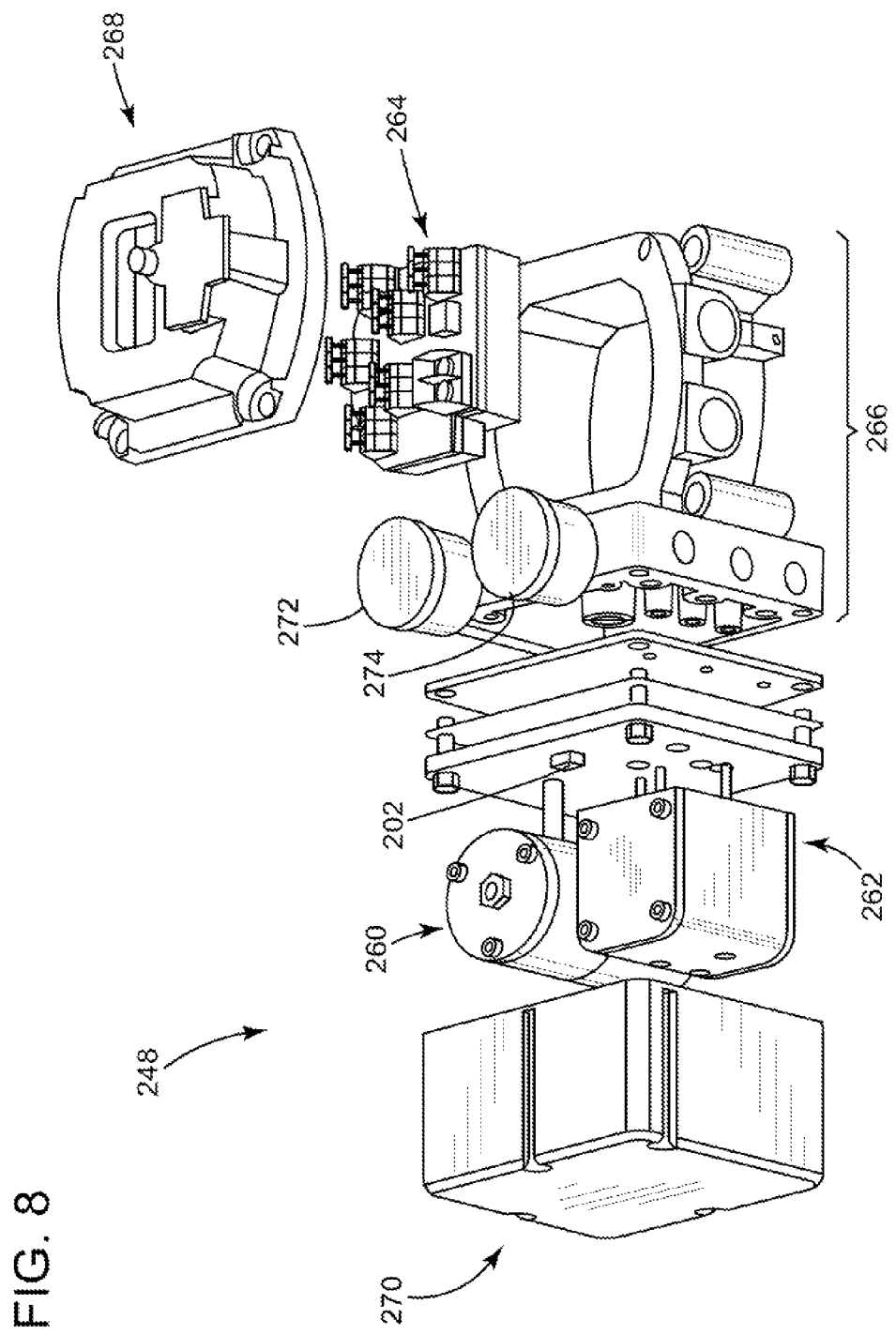
FIG. 8 depicts a perspective, exploded assembly view of an example of operative hardware for use to operate the valve device of FIG. 7.

FIGS. 7 and 8 illustrate an example of the valve assembly 204, also referred to as a control valve 246, for use in a process line. In FIG. 7, the control valve 246 includes a valve positioner 248 that receives the instrument gas, an actuator 250, and a fluid coupling 252 with a body 254 that has a first inlet/outlet 256 and a second inlet/outlet 258. The fluid coupling 252 can also include valve members (e.g., a stem, a plug, and a seat) that are found interior to the body 254 and, thus, not shown in the present view. This structure can modulate flow of the process fluid $F_P$ between the inlet/outlets 256, 258. During operation, the instrument gas stimulates the actuator 250 to move the valve elements disposed in the body 254. The feature changes the position of the elements (e.g., from a first valve position to a second valve position). The change in position modulates flow of the process fluid $F_P$ across the inlet/outlets 256, 258. In one implementation, the valve positioner 248 has components that regulate the flow of the instrument air to the actuator 250. This construction of the valve positioner 248 can change the position of the valve elements in response to one or more input control signals the valve positioner 248 receives from a remote device.

FIG. 8 depicts an example of the valve positioner 248 in exploded form. As shown in this diagram, the valve positioner 248 has a plurality of valve components (e.g., a converter component 260, a relay component 262, a processing component 264). The valve positioner 248 also has a housing 266. One or more covers (e.g., a first cover 268 and a second cover 270) can secure with the housing 266 to form an enclosure about the valve components. This enclosure protects the valve components from conditions that prevail in the environment surrounding the control valve 246 (FIG. 7). The valve positioner 248 also includes one or more gauges (e.g., a first gauge 272 and a second gauge 274) that can provide an indication of the flow conditions (e.g., pressure, flow rate, etc.) of the instrument gas that the valve positioner 248 uses to operate the valve in the control valve 246 (FIG. 7).

As noted above, operation of the valve positioner components 260, 262, 264 maintain the position of the valve elements in the body 254 (FIG. 7) to modulate flow of the process fluid $F_P$ across the inlet/outlets 256, 258 (FIG. 7). The measurement module 202 can integrate into the construction of the valve positioner 248 to provide localized information about the quality of the instrument gas. This construction can position at least part of the measurement module 202 inside enclosure of the covers 268, 270. In this manner, the valve positioner 248 can house all of the components necessary to monitor the quality of instrument gas that the valve components 260, 262, 264 will use to facilitate movement of the valve elements discussed above.

Figure 9:
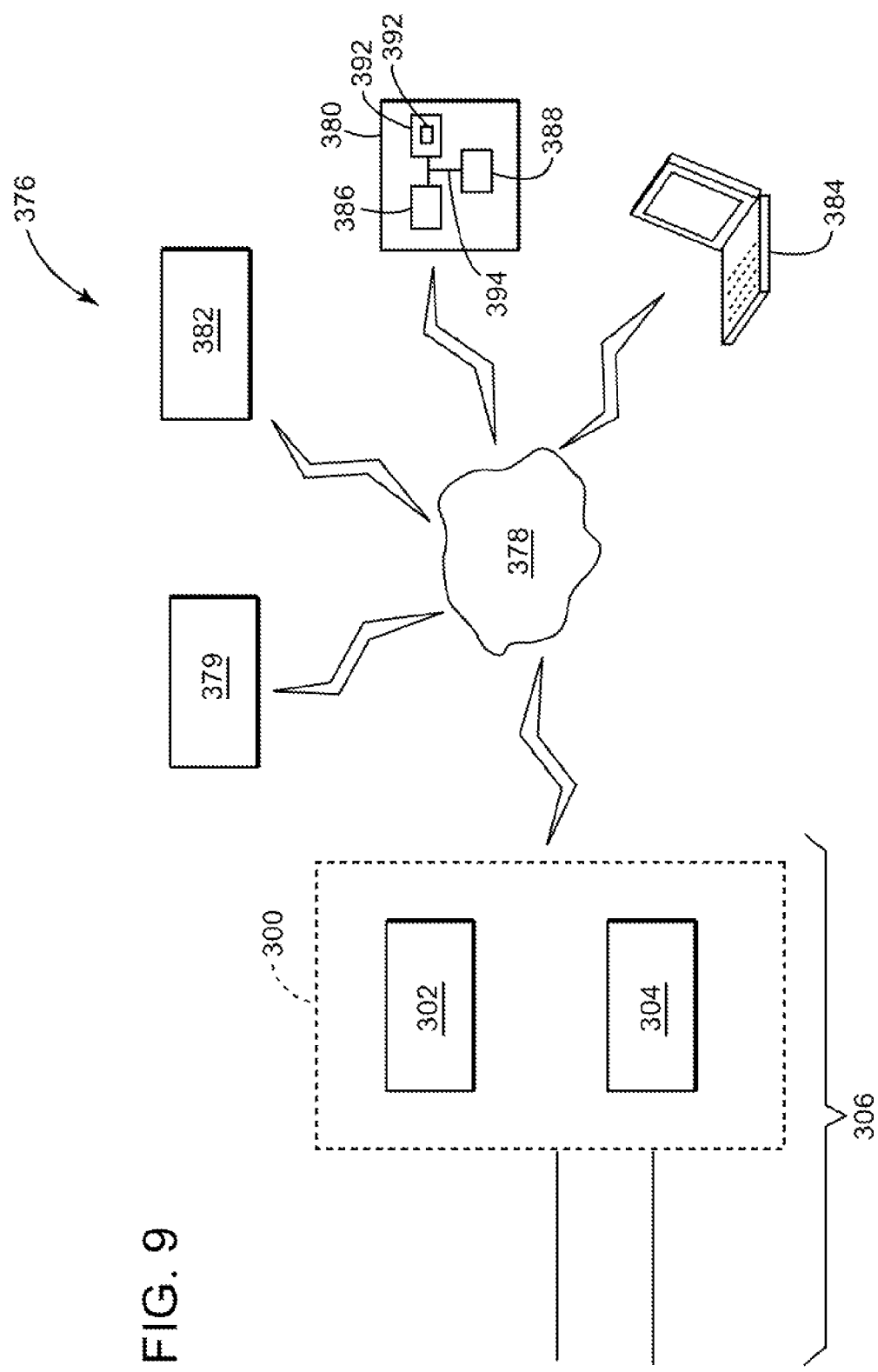
FIG. 9 depicts a schematic diagram of an exemplary embodiment of a system that can monitor quality of instrument gas for use by valves on a process line.

FIG. 9 depicts a schematic diagram of an exemplary embodiment of a system 300 for monitoring quality of instrument gas in a process facility or plant. The process line 306 couples with a network system 376 that has a network 378 that can deploy various wired and wireless constructions, as desired, to facilitate the exchange of data and information among the components. In one implementation, the network system 376 may incorporate a control server 379 that controls operation of the devices on the process line 306 via various protocols (e.g., HART, FOUNDATION Fieldbus, etc.). The network system 376 can also have one or more management servers 380, one or more external data servers 382, and one or more terminals 384. Examples of the terminal 384 can include a variety of computing devices (e.g., personal computers, workstations, laptop computers, tablet computers, smartphones, etc.) that an end user can utilize to interface with the central controller 380 and/or one or more components of the system 300.

The management server 380 can have a processor 386, control circuitry 388, and access to memory 390, which can store one or more executable instructions 392, e.g., in the form of software and firmware that are configured to be executed by a processor (e.g., the processor 386). The management server 380 can also includes busses 394 to couple components (e.g., processor 386, control circuitry 388, and memory 392) of the central controller 380 together. The busses 394 permit the exchange of signals, data, and information from one component of the central controller 380 to another. This disclosure also contemplates configurations in which one or more programs and/or executable instructions (e.g., executable instructions 392) are found on the external server 382. The management server 380 can access these remotely stored items to perform one or more functions disclosed herein. In one embodiment, a terminal 384 may communicate with the management server 380 and/or the network 378, e.g., to interface and/or to interact with the control server 379 and/or other components of the network system 376 and/or process line 306 and/or process facility in general, as desired.

FIG. 10 illustrates a flow diagram of a method 400 for identifying potential problems with a valve assembly on a process line. The method 400 includes, at step 402, receiving one or more inputs comprising raw sensor data that reflects a characteristic of instrument gas for use by the valve assembly. The method 400 also includes, at step 404, processing the one or more inputs to generate a contamination value that, in one example, represents a degree of contamination of the instrument gas. At step 406, the method 400 includes comparing the contamination value to one or more threshold values. The method 400 further includes, at step 408, generating an output. Examples of the output can include data that may include the raw sensor data, the contamination value, and/or one or more alerts having values that reflect the relationship between the contamination value and the threshold value.

The input (e.g., at step 402) may correspond to one or more signals (e.g., the output O) that arise from one or more sensor components (e.g., sensor component 224 of FIGS. 2, 3, 4, 5, and 6). Examples of the raw sensor data can reflect the presence of contaminants in the instrument gas that the valve assembly uses to modulate flow of the process fluid. This raw sensor data may, in one example, aggregate information about contamination over a period of time (also, "a sample period"). The aggregate information can illustrate changes, if any, in the characteristics of the instrument gas during operation. The sample period may encompass varying chronological values (e.g., minutes, hours, days, months, etc.).

The step of processing the one or more inputs (e.g., at step 404) can utilize this raw sensor data to quantify characteristics of the instrument gas. For example, the contamination value may be proportional to the amount of contamination. The processing step may include one or more steps for simply passing one of the raw sensor data values through, which would be appropriate, for example, if the sensor data naturally represents the degree of contamination. The processing steps may also include one or more steps for storing, integrate, and/or accumulating the raw sensor data over time.

The step of comparing the data to the one or more threshold values (e.g., at step 404) can use this information to identify and/or diagnose conditions with the instrument gas and the valve assembly. For example, the threshold values may include a first threshold value that reflects a maximum (and/or minimum) level for the characteristics; thus, in one example, deviation from the threshold value may indicate the onset of problems with the instrument gas. Interrogation of aggregated raw sensor data over the sample period may help to diagnose potential problems with the valve assembly. In another example, the threshold value may include a second threshold value that identifies one or more characteristics that are known to cause problems in the future. In this manner, deviation from the value of the threshold criteria may allow for pre-emptive efforts (e.g., replacing the all or part of the valve assembly, identifying the source of contamination, etc.) to mitigate risks to the valve assembly and/or the controlled process.

The contamination values (e.g., at step 406) and the alert values (e.g., at step 408) are useful to instruct the presence of these potential problems and to alert the process facility to the potential risks. Examples of the alert values may correspond to an alert, an alarm, and/or one or more other indicators (e.g., an LED on the valve assembly and/or other instrumentation on the control system) of problems that may arise as a result of degradation of the instrument gas. The output can convey instructions to prompt activation of this indicator. In one implementation, the alert values may provide a warning and/or critical warning that reflect the potential onset of problems with the valve assembly. In other implementations, the alert valves may indicate normal and/or acceptable quality (or other characteristics) for the instrument air.

Collectively, one or more of the steps of the method 400, and embodiments related to the method 400, can be coded as one or more executable instructions (e.g., hardware, firmware, software, software programs, etc.). These executable instructions can be part of a computer-implemented method and/or program, which can be executed by a processor and/or processing device. The processor may be part of the various components and systems, one or more of which may be adapted to execute these executable instructions, as well as to process inputs and to generate outputs.

Examples of some of the components can comprise computers and computing devices with processors and memory that can store and execute certain executable instructions, software programs, and the like. These control devices can be a separate unit, e.g., part of equipment that control valves and other components in a process facility. In other examples, these control devices integrate with the valve, e.g., as part of the hardware (e.g., the valve positioner) and/or software configured on such hardware. In still other examples, these control devices can be located remote from the valve, e.g., in a separate location where the control device can receive information from sensors, issue commands and instructions using wireless and wired communication via a network.

These control devices may have constructive components that can communicate amongst themselves and/or with other circuits (and/or devices), which execute high-level logic functions, algorithms, as well as executable instructions (e.g., firmware instructions, software instructions, software programs, etc.). Exemplary circuits of this type include discrete elements such as resistors, transistors, diodes, switches, and capacitors. Examples of a processor include microprocessors and other logic devices such as field programmable gate arrays ("FPGAs"), ARM microcontroller, and application specific integrated circuits ("ASICs"). Although all of the discrete elements, circuits, and devices function individually in a manner that is generally understood by those artisans that have ordinary skill in the electrical arts, it is their combination and integration into functional electrical groups and circuits that generally provide for the concepts that are disclosed and described herein.

The structure of the control devices can permit certain determinations as to selected configuration and desired operating characteristics that an end user might convey via the graphical user interface or that are retrieved or need to be retrieved by the device. For example, the electrical circuits of these control devices can physically manifest theoretical analysis and logical operations and/or can replicate in physical form an algorithm, a comparative analysis, and/or a decisional logic tree, each of which operates to assign the output and/or a value to the output that correctly reflects one or more of the nature, content, and origin of the changes in parameters that are reflected by the inputs to these control devices as provided by the corresponding control circuitry.

In one embodiment, a processor can also include state machine circuitry or other suitable components capable of controlling operation of the components as described herein. The memory includes volatile and non-volatile memory and can store executable instructions in the form of and/or including software (or firmware) instructions and configuration settings. Each of the control circuitry can embody stand-alone devices such as solid-state devices. Examples of these devices can mount to substrates such as printed-circuit boards and semiconductors, which can accommodate various components including a processor, memory, and other related circuitry to facilitate operation of other devices and/or components.

However, although processor, memory, and circuitry might include discrete circuitry and combinations of discrete components, this need not be the case. For example, one or more of these components can comprise a single integrated circuit (IC) or other component. As another example, a processor can include internal program memory such as RAM and/or ROM. Similarly, any one or more of functions of these components can be distributed across additional components (e.g., multiple processors or other components).

Moreover, as will be appreciated by one skilled in the art, aspects of the present disclosure may be embodied as a system, method, or computer program product. Accordingly, aspects of the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present disclosure may take the form of a computer program product embodied in one or more computer readable medium(s) having computer readable program code embodied thereon.

Any combination of one or more computer readable medium(s) may be utilized. The computer readable medium may be a non-transitory computer readable signal medium or a non-transitory computer readable storage medium. Examples of a computer readable storage medium include an electronic, magnetic, electromagnetic, and/or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing. This program code may be written in any combination of one or more programming languages, including an object oriented programming language and conventional procedural programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The executable or computer program instructions may be provided to a processor of a general purpose computer, special purpose computer, or other programmable data processing apparatus to produce a machine, such that the instructions, which execute via the processor of the computer or other programmable data processing apparatus. The computer program instructions may also be stored in and/or on a computer readable medium that can direct a computer, other programmable data processing apparatus, or other devices to function in a particular manner.

In light of the foregoing, the systems and methods discussed above monitor characteristics of the instrument gas in proximity to the valve assembly. These embodiments can data that reflects these characteristics to identify potential problems or deliver data to the control system for further processing and analysis. The components of the system can generate outputs that reflect the quality of the instrument gas; as to, for example, levels of particulates and other contaminants, humidity, temperature, and the like. Processing of data and information in the output can help to diagnose changes in the quality of the operating fluid and, moreover, the impact that the changes in quality can have on operation of control valves and devices on the process line. This diagnosis is useful to predict a time frame during which a control valve and components associated therewith might fail and/or require maintenance before the control valve manifests significant problem that are detrimental to a process line.

Thus, a technical feature afforded embodiments contemplated herein is to quantify characteristics of instrument gas for control valves (and related devices) used to modulate flow of a working fluid. As set forth above, these embodiments include a measurement module that generates outputs with data that reflects characteristics of the instrument gas from samples upstream of the control valve. This data can render, inter alia, indicators that can alert as to the status, both present and future status, of the instrument and the devices on a process line.

As used herein, an element or function recited in the singular and proceeded with the word "a" or "an" should be understood as not excluding plural said elements or functions, unless such exclusion is explicitly recited. Furthermore, references to "one embodiment" of the claimed invention should not be interpreted as excluding the existence of additional embodiments that also incorporate the recited features.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A system, comprising:
    a valve assembly comprising a pneumatic actuator, a fluid coupling with valve elements coupled to the pneumatic actuator, and a valve positioner coupled to the pneumatic actuator;
    a first fluid supply providing a process fluid to the fluid coupling;
    a second fluid supply with a fluid supply line that provides an instrument gas to the valve positioner; and
    a measurement module coupled to the fluid supply line, the measurement module having a connector that couples electrically with the valve positioner, the measurement module comprising a housing enclosing a flow pathway with an inlet and an outlet, both being formed in the housing so that the outlet exhausts to environment, a chamber spaced apart from the flow pathway to receive the instrument gas, a sensor component disposed in the chamber, and a sample line coupled to one side of the chamber and to the flow pathway between the inlet and the outlet,
    wherein the sensor component is configured to generate an output that reflects a characteristic of the instrument gas in the chamber,
    wherein the inlet of the flow pathway couples with the fluid supply line to direct a first sample of the instrument gas out of the fluid supply line to the inlet of the flow pathway with the flow pathway spaced apart from the fluid supply line,
    wherein the first sample originates from a location on the fluid supply line that is upstream of each component in the valve positioner that regulates a position of the actuator on the valve assembly, and
    wherein the sample line directs a second sample out of the first sample in the flow pathway to the chamber.

2. The system of claim 1, wherein the location of the first sample is within two feet or less of the one or more components of the valve positioner.

3. The system of claim 1, wherein the measurement module is configured to secure to one or more structures of the valve assembly.

4. The system of claim 1, wherein the measurement module integrates with the valve positioner.

5. The system of claim 1, wherein the sensor component comprises a first sensor element and a second sensor element in position on an axis that extends through the chamber.

6. The system of claim 5, wherein the first sensor element comprises a source that generates light and the second sensor element comprises a detector that generates an output in response to the light.

7. The system of claim 1, wherein the connector is configured to exchange a signal with one or more components of the valve positioner, and wherein the signal comprises the output that reflects the characteristic of the instrument gas in the chamber.

8. The system of claim 1, further comprising a central controller including executable instructions that are configured to cause the central controller to:
    receive one or more inputs comprising raw sensor data that reflects the characteristic of instrument gas for use by the valve assembly;

process the one or more inputs to generate a contamination value;

compare the contamination value to one or more threshold values; and generate an output with data that reflects the relationship between the contamination value and the threshold value.

9. The system of claim 8, wherein the data comprises one or more alert values that correspond to problems that arise as a result of degradation of the instrument gas.

10. The system of claim 1, wherein the sensor component comprises an opto-electronic sensor.

11. The system of claim 1, wherein the characteristic identifies a level of contamination in the instrument gas.

12. The system of claim 1, wherein the valve positioner has hardware that integrates the component, the hardware including a processing component, wherein the connector electrically connects with the hardware of the valve positioner to allow the processing component to receive the output from the sensor component.

13. The system of claim 12, wherein the measurement module is disposed outside of the valve positioner.

14. The system of claim 12, wherein the processing component is configured to access executable instructions, the executable instruction comprising one or more executable instructions for:

receiving one or more inputs comprising raw sensor data that reflects a characteristic of instrument gas for use by the valve assembly;

processing the one or more inputs to generate a contamination value;

comparing the contamination value to one or more threshold values; and generating an output with data that reflects the relationship between the contamination value and the threshold value.

15. The system of claim 14, wherein the data comprises one or more alert values that correspond to problems that arise as a result of degradation of the instrument gas.

16. The system of claim 1, wherein the sensor component comprises a photo-optical sensor.

17. The system of claim 16, further comprising a processing component configured to access executable instructions, the executable instruction comprising one or more executable instructions for:

receiving one or more inputs comprising raw sensor data that reflects a characteristic of instrument gas for use by the valve assembly;

processing the one or more inputs to generate a contamination value;

comparing the contamination value to one or more threshold values; and generating an output with data that reflects the relationship between the contamination value and the threshold value.

18. The system of claim 17, wherein the data comprises one or more alert values that correspond to problems that arise as a result of degradation of the instrument gas.

* * * * *